(12) United States Patent
Cabrera et al.

(10) Patent No.: US 9,389,111 B2
(45) Date of Patent: Jul. 12, 2016

(54) DYNAMIC-ADAPTIVE VAPOR REDUCTION SYSTEM AND METHOD

(75) Inventors: Rafael A. Cabrera, Greenwood, SC (US); Jaime Sanchez, Greenwood, SC (US)

(73) Assignee: Measurement Technology Group, Inc., Chevy Chase, MD (US)

( * ) Notice: Subject to any disclaimer, the term of this patent is extended or adjusted under 35 U.S.C. 154(b) by 1089 days.

(21) Appl. No.: 12/721,731

(22) Filed: Mar. 11, 2010

(65) Prior Publication Data

US 2011/0220213 A1   Sep. 15, 2011

(51) Int. Cl.
| | |
|---|---|
| G01F 1/84 | (2006.01) |
| G01F 15/00 | (2006.01) |
| G01F 15/02 | (2006.01) |
| G01N 9/00 | (2006.01) |
| G01N 9/32 | (2006.01) |

(52) U.S. Cl.
CPC ............ *G01F 1/8472* (2013.01); *G01F 1/8413* (2013.01); *G01F 15/001* (2013.01); *G01F 15/005* (2013.01); *G01F 15/02* (2013.01); *G01F 15/026* (2013.01); *G01N 9/002* (2013.01); *G01N 9/32* (2013.01); *Y10T 137/0335* (2015.04); *Y10T 137/7759* (2015.04)

(58) Field of Classification Search
USPC ................................................ 137/14, 487.5
See application file for complete search history.

(56) References Cited

U.S. PATENT DOCUMENTS

| | | | | |
|---|---|---|---|---|
| 4,718,443 A | * | 1/1988 | Adney et al. ........................ 137/8 |
| 5,062,446 A | * | 11/1991 | Anderson ....................... 137/468 |
| 5,804,741 A | | 9/1998 | Freeman | |
| 5,927,321 A | | 7/1999 | Bergamini | |
| 5,975,126 A | * | 11/1999 | Bump et al. ................ 137/487.5 |
| 6,471,487 B2 | | 10/2002 | Keilty et al. | |
| 7,114,517 B2 | | 10/2006 | Sund et al. | |
| RE40,095 E | * | 2/2008 | Dutton ..................... 73/861.356 |
| 7,344,297 B2 | * | 3/2008 | Urquhart ...................... 366/132 |
| 7,421,350 B2 | * | 9/2008 | Duffill et al. ..................... 702/50 |
| 7,523,647 B2 | * | 4/2009 | Scott ............................ 73/61.44 |
| 7,592,033 B2 | * | 9/2009 | Buckley et al. .................... 427/8 |
| 7,693,606 B2 | * | 4/2010 | Ahmad et al. ................ 700/282 |
| 7,908,097 B2 | * | 3/2011 | Duffill et al. ..................... 702/45 |
| 7,971,604 B2 | * | 7/2011 | McDonald et al. ........ 137/487.5 |
| 8,356,623 B2 | * | 1/2013 | Isobe et al. ..................... 137/486 |
| 2002/0033043 A1 | * | 3/2002 | Dutton et al. ................ 73/61.44 |
| 2002/0100505 A1 | * | 8/2002 | Keilty et al. ............... 137/487.5 |
| 2003/0136185 A1 | * | 7/2003 | Dutton et al. ................ 73/61.44 |
| 2005/0016292 A1 | * | 1/2005 | Dutton et al. ............. 73/861.03 |
| 2009/0107218 A1 | * | 4/2009 | Latham ....................... 73/61.44 |

* cited by examiner

*Primary Examiner* — Matthew W Jellett
(74) *Attorney, Agent, or Firm* — Dority & Manning, P.A.

(57) ABSTRACT

A system and method for improved flow measurements for LCG, such as liquid petroleum gas (LPG), is disclosed. Embodiments of the present technology detect the presence of a vapor in a fluid flowing in a mass flow meter. A control valve is then adjusted to provide enough back pressure to prevent the measured liquid from flashing and to reduce the presence of vapor in the fluid flowing in the mass flow meter. By keeping the fluid in liquid form, the present technology reduces the vapor flowing in the mass flow meter, increasing the accuracy of mass flow and other measurements. Utilizing a similar principle of vapor detection, embodiments of the present technology provide for improved average parameter value calculation, such as average density calculations and equivalent liquid volume calculations.

6 Claims, 3 Drawing Sheets

DYNAMIC-ADAPTIVE VAPOR REDUCTION SYSTEM AND METHOD

FIELD OF THE INVENTION

The present technology generally relates to fluid flow measurement systems and more particularly to reducing the presence of vapor and its detrimental effects in a fluid during flow measurements performed by a mass flow meter. The methods discussed hereon are not fluid dependent, but vapor-presence dependent; therefore, the methods apply to all liquefied compressed gases (LCG).

BACKGROUND OF THE INVENTION

Performing fluid flow measurements for LCG, such as liquid petroleum gas (LPG), entails a broader set of challenges that are not present in the measurement of other fluids. For the product to remain in a liquid state, LCG require the pressure of the fluid system to be maintained above the vapor pressure (i.e., the pressure at which a liquid-gas equilibrium occurs) for the fluid. If the pressure in the fluid system drops below the characteristic vapor pressure of the product, the liquid flashes (evaporates) to its vapor or gaseous state.

The presence of a mixture of a vapor and a liquid in certain mass flow meters, such as Coriolis mass flow meters, can detrimentally affect the accuracy of the mass flow measurements and other measurements. For example, the mixture of gas and liquid in the fluid flowing in a Coriolis mass flow meter causes a decrease in the amplitude of vibration and a corresponding decrease in measurement accuracy. Error in density measurements is another detrimental effect of the presence of gas in fluid flow measurements. Because the average density of a liquid is greater than the average density of a gas, the presence of a mixture of gas and liquid in the fluid will yield an average density measurement that is too heavy for a gas and too light for a liquid. If such density measurement is used to convert measured mass to volume, the calculated volume could have a significant error when compared to calibrated volumetric references.

Existing flow measurement systems rely on ancillary devices, such as vapor eliminator tanks, to provide vapor reduction. Vapor eliminator tanks can be used to trap some of the vapor originating before the eliminator tanks, but do not typically control vapor forming after the eliminator due to critical pressure drops. Another approach uses differential pressure valves to control line pressure, but the settings on the differential pressure valves are limited to a particular product with a particular vapor pressure. Therefore, such approach relies on the concept that the product's vapor pressure characteristics will remain unchanged. Other technologies use pressure transducers, control valves, and programmable logic controllers to control the line pressure. Such can be a technically effective alternative, but requires expensive equipment and extensive support.

U.S. Pat. No. 6,471,487 to Keilty, et al. discloses a fluid delivery system that includes a Coriolis mass flow meter, a pump, a recirculation valve, and/or a back pressure valve. The fluid delivery system prevents the measurement of a multiphase fluid flow without the need for an air eliminator and strainer. If the measured density value exceeds one or more comparison values, the flow meter automatically shuts down the pump and closes the back pressure valve to stop the delivery of the fluid product from the fluid source to the destination to prevent the measurement of a multiphase fluid flow. However, this method requires extra piping for the recirculation path.

Other examples of U.S. patents relating to Coriolis flow meter technology include U.S. Pat. No. 7,114,517 to Sund, et al., U.S. Pat. No. 5,927,321 to Bergamini, and U.S. Pat. No. 5,804,741 to Freeman.

The disclosures of the foregoing patents are fully incorporated herein for all purposes.

There is a need for a fluid flow measurement system and methodology that reduces the presence of vapor using a minimal amount of equipment and minimal cost. While various methodologies have been developed for reducing detrimental effects caused by the presence of vapor in fluid flow measurement systems, no design has emerged that generally encompasses all of the desired characteristics, in an adaptive and dynamic form, as hereafter presented in accordance with the subject technology.

SUMMARY OF THE INVENTION

In view of the recognized features encountered in the prior art and addressed by the present subject matter, improved system and methodology are presently disclosed for dynamic-adaptive vapor reduction in a fluid flow measurement system. It is to be understood that the present subject matter equally encompasses both system (apparatus) and methodology.

In an exemplary configuration, a fluid flow measurement system and methodology that reduces the presence of a vapor in a fluid being measured in a mass flow meter is provided.

In accordance with aspects of certain embodiments of the present disclosure, control flow valves are used to provide back pressure to prevent LCG from flashing while flowing in a mass flow meter.

In accordance with yet further aspects of certain embodiments of the present disclosure, the flow measurement system and methodology identifies the density of a fluid in a liquid and gas flow mixture environment.

In accordance with yet further aspects of certain embodiments of the present disclosure, the flow measurement system and methodology determines an equivalent liquid volumetric total from a dry vapor flow measurement.

One exemplary embodiment of the present disclosure is directed to a fluid flow measurement system. The system includes a mass flow meter configured to measure at least one parameter of a fluid flowing in the mass flow meter and a control valve located downstream of the mass flow meter. The control valve provides a back pressure on the fluid flowing in the mass flow meter. The system further includes a controller configured to detect a vapor in the fluid flowing in the mass flow meter. The controller adjusts the control valve in response to detecting the vapor in the fluid so as to reduce the vapor in the fluid flowing in the mass flow meter.

Variations and modifications can be made to such exemplary embodiment of the present disclosure. For instance, in one variation of this exemplary embodiment, the mass flow meter may provide an output signal indicative of at least one parameter measured by the mass flow meter and the controller may be further configured to detect a vapor in the fluid flowing in the mass flow meter based at least in part from the output signal.

In another variation of such exemplary embodiment, the mass flow meter may be a Coriolis mass flow meter that includes both single and multiple tube transducers having an amplitude of vibration inversely proportional to the concentration of a minority state of the fluid (in a liquid+vapor mixture) flowing in the meter tubes. The Coriolis mass flow meter may provide an output signal having an output signal amplitude proportional to the amplitude of vibration of the meter tubes. The controller may be further configured to detect a vapor in the fluid flowing in the mass flow meter based on the output signal amplitude.

In yet another variation of such exemplary embodiment, the controller may adjust the control valve to provide a back pressure sufficient to prevent the fluid flowing in the mass flow meter from flashing. In still another variation of such exemplary embodiment, the controller may adjust the control valve to provide a maximum flow rate with enough back pressure to prevent the fluid flowing in the mass flow meter from flashing.

In still a further variation of such exemplary embodiment, the control valve may have a closed position and the controller may be further configured to prevent the control valve from operating in the closed position when fluid is flowing in the mass flow meter.

Another exemplary embodiment of the present disclosure is directed to a method of reducing the amount of vapor in a fluid flowing in a mass flow meter. The method includes flowing a fluid into a mass flow meter; measuring at least one parameter of the fluid at the mass flow meter; detecting a vapor in the fluid flowing in the mass flow meter; and adjusting a control valve located downstream of the mass flow meter in response to detecting a vapor in the fluid flowing in the mass flow meter such that the amount of vapor in the fluid flowing in the mass flow meter is reduced.

In a variation of such exemplary embodiment, the method may include providing an output signal from the mass flow meter indicative of the at least one parameter measured by the mass flow meter; and detecting a vapor in the fluid flowing in the mass flow meter from the output signal.

In another variation of such exemplary embodiment, the mass flow meter can be a Coriolis mass flow meter having an amplitude of vibration inversely proportional to the percentage of minority fluid flowing in said meter tubes. The method can include providing an output signal having an output signal amplitude proportional to the amplitude of vibration of the meter tubes; and detecting a vapor in the fluid flowing in the mass flow meter based on the output signal amplitude.

In still another variation of such exemplary embodiment, the step of adjusting a control valve may comprise adjusting the control valve to provide a back pressure sufficient to prevent the fluid flowing in the mass flow meter from flashing. In still a further variation of such exemplary embodiment, the step of adjusting a control valve may comprise adjusting the control valve to provide a maximum flow rate with enough back pressure to prevent the fluid flowing in the mass flow meter from flashing.

In a further variation of such exemplary embodiment, the control valve may have a closed position and the method may further include preventing the control valve from operating in the closed position when fluid is flowing in the mass flow meter.

In still a further variation of such exemplary embodiment, the method can include monitoring the pressure of the fluid and opening a back pressure valve located downstream of the mass flow meter to allow fluid to flow into the mass flow meter when the pressure of the fluid exceeds a vapor pressure for the fluid.

A further exemplary embodiment of the present disclosure is directed to a method of determining an average parameter value of a fluid. The method includes flowing fluid in a mass flow meter; measuring at least one parameter value for the fluid flowing in the mass flow meter; determining whether a vapor is present in the fluid flowing in the mass flow meter; assigning a weight value to the at least one parameter value based at least in part on the presence of a vapor in the fluid flowing in the mass flow meter; and calculating a weighted average parameter value using the at least one parameter value and the weight value assigned to the at least one parameter value.

In a variation of such exemplary embodiment, the step of assigning a weight value may include assigning a first weight value to the at least one parameter value if a vapor is determined to be present in the mass flow meter and assigning a second weight value to the at least one parameter value if a vapor is not determined to be present in the mass flow meter, preferably with the first weight value being less than the second weight value. For instance, in a particular embodiment, the first weight value can be approximately zero.

In another variation of such exemplary embodiment, the mass flow meter may be a Coriolis mass flow meter and the method may further include monitoring a driver signal provided to the Coriolis mass flow meter; determining whether the driver signal is saturated; and determining that a vapor is present in the fluid flowing in the Coriolis mass flow meter when the driver signal is saturated.

In another variation of such exemplary embodiment, the average parameter value may comprise the average density of the fluid flowing in the mass flow meter. In yet another variation of such exemplary embodiment, the method may include measuring the total mass of the fluid flowing in the mass flow meter and determining an equivalent liquid volume, in a mixture of liquid, liquid+vapor, and/or vapor, for the fluid flowing in the mass flow meter by dividing the total mass flowing in the mass flow meter by the average density.

Additional objects and advantages of the present subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments and uses of the present subject matter without departing from the spirit and scope of the present subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

Figure 1:
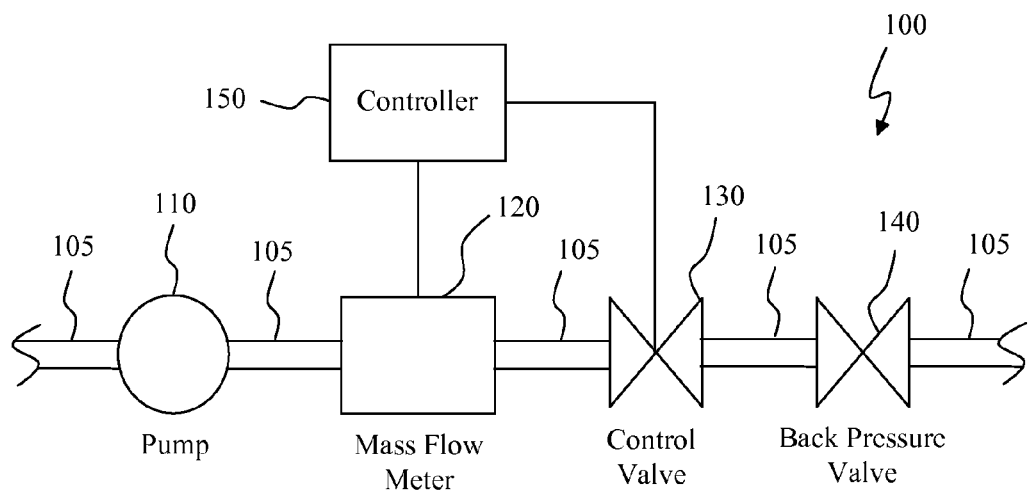
FIG. 1 is a fluid flow diagram (with intended flow illustrated left to right) of a fluid flow measurement system according to one exemplary embodiment of the present disclosure.

Repeat use of reference characters throughout the present specification and appended drawings is intended to represent same or analogous features, elements, or steps of the present subject matter.

DETAILED DESCRIPTION OF THE PREFERRED EMBODIMENTS

Reference now will be made in detail to embodiments of the present subject matter, one or more examples of which are illustrated in the drawings. Each example is provided by way of explanation of the present subject matter, not limitation of the present subject matter. In fact, it will be apparent to those skilled in the art that various modifications and variations can be made in the present subject matter without departing from the scope or spirit of the present subject matter. For instance, features illustrated or described as part of one embodiment, can be used with another embodiment to yield a still further embodiment. Thus, it is intended that the present subject matter encompass such modifications and variations as come within the scope of the appended claims and their equivalents.

In general, the present technology provides for improved flow measurements for LCG, such as LPG. Embodiments of the present technology detect the presence of a vapor in a fluid flowing in a mass flow meter. A control valve is then adjusted to provide enough back pressure to prevent the measured liquid from flashing and to reduce the presence of vapor in the fluid flowing in the mass flow meter. By keeping the fluid in liquid form, the present technology reduces the vapor flowing in the mass flow meter, increasing the accuracy of mass flow and other measurements.

Utilizing a similar principle of vapor detection, embodiments of the present technology provide for improved average parameter value calculation, such as average density measurements and equivalent liquid volumetric calculations in mixed (liquid+vapor) states. The average density measurements are performed pursuant to a weighted average algorithm that places weight on the individual mass flow measurements. A weighted average algorithm gives little to zero weight to density measurements performed when the system and methodology detects the presence of a vapor in the measured fluid, reducing the effect on averaging if there is a vapor in the measured fluid. In the measurement of LCG in its gaseous form, the average density calculation can be used to provide a more accurate Equivalent Liquid Volume calculation by dividing the total measured mass of the gas state fluid by the average density of the previously measured [pure] liquid state calculated according to the weighted average algorithm.

FIG. 1 illustrates an exemplary flow measurement system generally 100 according to one exemplary embodiment of the present disclosure. Flow measurement system 100 can be used as part of a fluid delivery system for a volatile fluid, such as LPG. Flow measurement system 100 determines or measures a variety of parameters for a fluid flowing in flow measurement system 100, including for instance, mass flow rate, volume flow rate, average line temperature, average density, observed specific gravity, standard specific gravity (60° F.), volume correction factor, mass total, gross volume total, net volume total, etc. The values for any of the above parameters can be used as part of an inventory management system for a fluid delivery system or for other suitable purposes.

As illustrated, flow measurement system 100 can include a pump 110, a mass flow meter 120, a control valve 130, and a back pressure valve 140. The various components of the flow measurement system 100 can be coupled together using piping 105. Those of ordinary skill in the art, using the disclosures provided herein, should understand that various different types of piping can be used to connect the various components of flow measurement system 100 as a matter of design choice and that the present disclosure is not limited to any particular kind or configuration of piping 105.

Flow measurement system 100 receives a fluid from a fluid source such as a storage tank or tank truck. Pump 110 is used to provide the fluid with a desired flow rate from the fluid source. Any pump, compressor, or other device can be used to provide the fluid with a desired flow rate into the mass flow meter. Preferably, the pump 110 is sized to provide the fluid with a flow rate that matches the flow rating of the mass flow meter 120.

Figure 2:
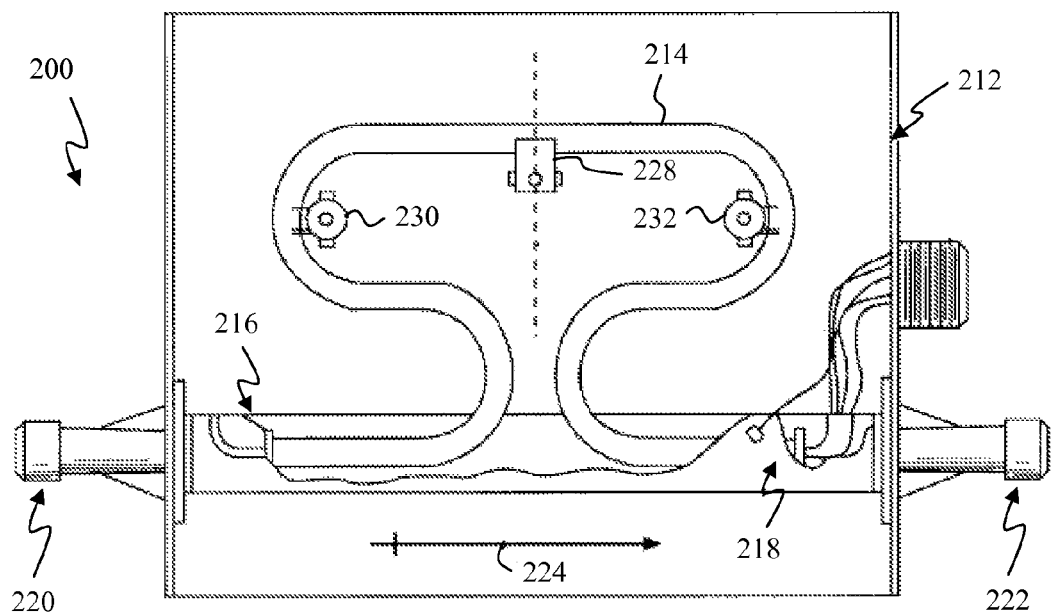
FIG. 2 provides a side elevational view, in partial cutaway, of an exemplary Coriolis mass flow meter that can be used in accordance with exemplary embodiments of the present disclosure.

The fluid is provided through pump 110 to mass flow meter 120. Mass flow meter 120 is used to measure one or more parameters of the fluid and provides one or more output signals indicative of the measured parameters. A typical mass flow meter 120 will provide a mass flow measurement and a density measurement for the fluid flowing in the mass flow meter. In one exemplary embodiment, mass flow meter 120 can be a Coriolis mass flow meter. Details of an exemplary Coriolis mass flow meter generally 200 are represented in FIG. 2. The construction and operation of a Coriolis mass flow meter are known in the art and are exemplified in U.S. Pat. No. 5,804,741, which is incorporated herein by reference.

Briefly, FIG. 2 provides a side elevational view, with partial cross section, of the internal structure of a representative Coriolis mass flow meter 200. Such meter 200 has a generally rectangular casing 212 within which are contained a pair of meter tubes or fluid flow conduits. An exemplary one of such meter tubes 214 is shown by the partial sectional view of FIG. 2. Such meter tube 214 has an inlet portion generally 216 and an outlet portion generally 218 respectively associated with inlet and outlet fluid conduit connections 220 and 222. As understood by those of ordinary skill in the art, manifolds or other elements are used to split fluid flow entering connection 220 into two separate pathways directed to the respective meter tubes. At the outlet end, flows from the respective conduits are combined for emerging together via connection 222. Hence, the general flow direction within device 200 is in the direction of arrow 224.

Meter tubes may be generally an omega shape as illustrated in FIG. 2, or may assume other shapes. Meter tubes are selected and appropriately mounted in mass flow meter 200 so as to have substantially the same mass distribution, moments of inertia, and elastic modules about their respective bending axes. The respective meter tubes are mounted within the mass flow meter so as to be parallel with each other between there respective end portions when not in use. In accordance with well known principles, a driver signal is provided to driver generally 228 to cause the meter tubes to vibrate. When there is no mass flow through the meter tubes, the meter tubes oscillate with each other with identical phase. As fluid begins to flow in the meter tubes, Coriolis accelerations cause the signals between sensors 230 and 232 to "shift" out of phase. The phase on the inlet side of the meter tubes lags the driver 228. The phase on the outlet side of the meter tubes leads the driver 228. The sensors 230 and 232 produce sinusoidal signals representative of the motion of the meter tubes. The phase difference between the sensor signals is proportional to the mass flow of the fluid through the meter tubes. The frequency of vibration of the meter tubes is inversely proportional to the density of the fluid flowing in the meter tubes 214. Thus, the Coriolis mass flow meter 200 is capable of providing an output signal(s) indicative of the mass rate of the fluid flowing in the mass flow meter 200 as well as the density of the fluid flowing in the mass flow meter 200.

Coriolis mass flow meters are able to measure liquids and gases accurately, without the need of re-calibration, as long as the percentage of the minority state of the fluid (e.g., vapor in the measurement of liquids) is kept below about 3%-5% by volume. In a Coriolis mass flow meter, the presence of a vapor in the fluid flowing in the meter tubes causes a decrease in the amplitude of vibration of the meter tubes, which correspondingly causes a decrease in measurement accuracy.

To reduce the detrimental effects caused by the presence of vapor flowing in mass flow meter 120, a control valve 130 is connected downstream of mass flow meter 120 to regulate the back pressure on the fluid flowing in the mass flow meter. Control valve 130 is regulated by controller 150 in response to the presence of a vapor in the fluid so as to increase or decrease the back pressure applied on the fluid. An increase in back pressure accelerates the condensation of the vapor in contact with the cooler liquid by reducing the volume of the vapor in the fluid stream, and, if the back pressure is maintained above the vapor pressure of the liquid, prevents formation (flashing) of vapor upstream of the valve.

Those of ordinary skill in the art, using the disclosures provided herein, should readily understand that the controller 150 can be any of a variety of analog or digital devices that can be used to implement the control methods according to embodiments of the present disclosure. For instance, controller 150 can include a processor configured to execute software or hardware instructions to regulate the back pressure provided by control valve 130. The controller 150 can be a part of the internal electronics of mass flow meter 120 or can be separate from mass flow meter 120. In a particular embodiment, the controller 150 can use a proportional-integral-derivative routine that uses an output signal provided by the mass flow meter to regulate the back pressure provided by the control valve 130. However, other control routines can be utilized to regulate control valve 130 without deviating from the spirit and scope of the present disclosure. For instance, as will be appreciated by those of ordinary skill in the art from the disclosures provided herein, controller 150 can similarly use a proportional, proportional-integral, or proportional-derivative control routine to regulate control valve 130.

Back pressure valve 140 is used to provide the fluid with sufficient pressure such that the fluid flowing into the mass flow meter is initially in a liquid state. In particular, as pump 110 begins providing pressure to the fluid, back pressure valve 140 can be used to hold the fluid line closed until the pressure of the fluid exceeds the vapor pressure of the fluid. Such approach will prevent the fluid from flashing into the vapor state prior to opening the back pressure valve 140 and flowing the fluid into the mass flow meter 120. Pressure alone will reduce, not eliminate, the volume of vapor. Various other devices can be used to apply pressure to the fluid before flowing the fluid into mass flow meter 120. For instance, in alternative configurations, a differential pressure switch and solenoid valve can replace the back pressure valve 140. However, backpressure valve 140 alone is not sufficient to control flashing in conditions where the vapor pressure varies significantly as in the case of consecutive measurements of fluids with different vapor pressures. E.g.: A backpressure valve that is adjusted to suppress flashing, at optimal flow, for low vapor pressure fluids will not suppress flashing when use with high vapor pressure fluids. In such cases the mentioned Dynamic-Adaptive system is necessary.

Figure 3:
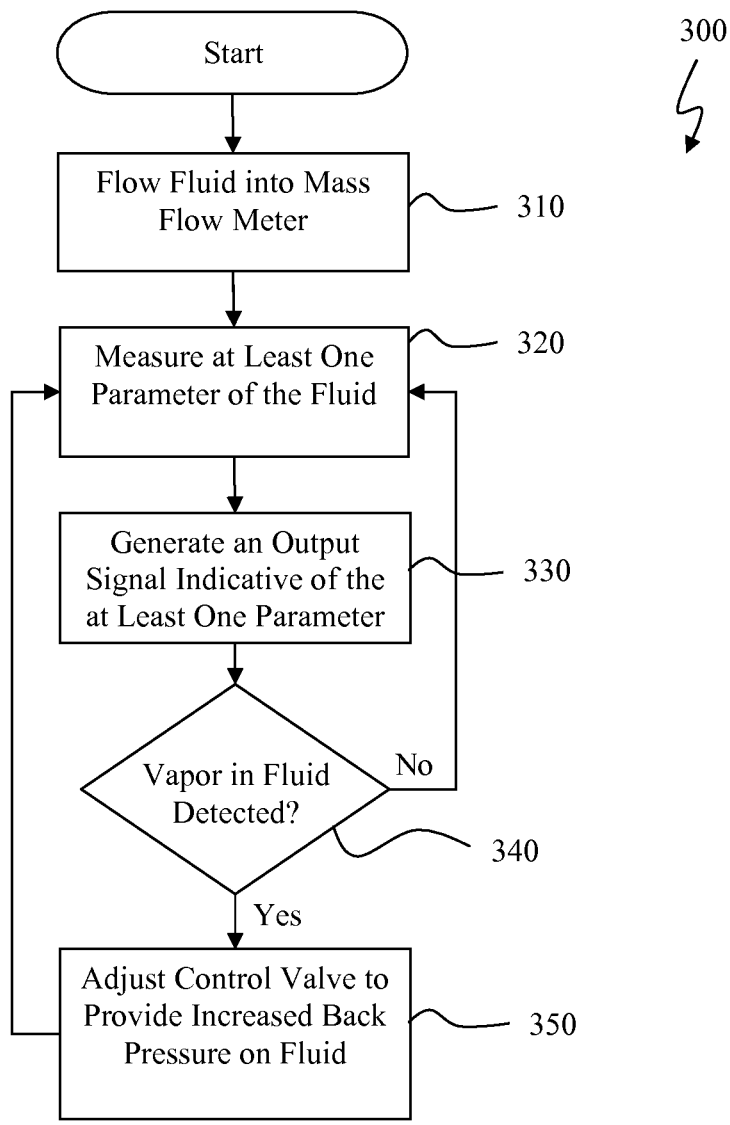
FIG. 3 provides a flow diagram of an exemplary method according to one embodiment of the present disclosure.

With reference now to FIG. 3, a present exemplary operation of fluid flow measurement system 100 will now be discussed in additional detail. At block 310, fluid is provided to mass flow meter 120. Fluid can be provided to mass flow meter 120 by connecting a fluid source, such as a storage tank or tank truck, to the flow measurement system 100 and by using pump 110 to provide the fluid with a suitable flow rate. The back pressure valve 140 can be initially closed until the pressure builds to a pre-set value that exceeds the vapor pressure of the fluid, causing most of the fluid to condense to a liquid state. The fluid can be provided to the mass flow meter 120 by opening the back pressure valve 140.

At block 320, the mass flow meter 120 measures at least one parameter of the fluid flowing in the mass flow meter. This parameter can be, for instance, the mass flow of the fluid flowing in the mass flow meter 120 or the density of the fluid flowing in the mass flow meter 120. The mass flow and density measurement can be used to calculate a variety of other parameters, including volume flowrate, average line temperature, average density, observed specific gravity, standard specific gravity (60° F.), volume correction factor, mass total, gross volume total, net volume total, etc.

At block 330, the mass flow meter 120 generates at least one output signal indicative of the measured parameter of the fluid. For instance, if mass flow meter 120 is a Coriolis mass flow meter, the mass flow meter 120 can provide sinusoidal output signals representative of the motion of the meter tubes. The phase difference between the sensor signals is proportional to the mass flow of the fluid through the meter tubes. The frequency of vibration of the meter tubes is inversely proportional to the density of the fluid flowing in the meter tubes. The amplitude of vibration is inversely proportional to the percentage of concentration of the minority fluid (vapor in a liquid+vapor mixture).

At block 340, the presence of a vapor is detected in the fluid. The presence of a vapor can be detected from the output signal provided by the mass flow meter 120. For instance, in a particular embodiment, the methodology 300 detects the presence of a vapor in the fluid flowing in the mass flow meter by monitoring the amplitude of vibration of the Coriolis meter tubes. A drop in the amplitude of vibration of the meter tubes and the corresponding drop in the amplitude of the output signal accompanies a drop in density of the fluid and therefore the presence of a vapor. If there is no reduction in the amplitude of vibration, there is no significant presence of vapor flowing in the fluid and the mass flow meter 120 will continue to perform parameter measurements of the fluid without any adjustments to control valve 130.

If a reduction in vibration amplitude is detected, the methodology 300 can determine that a significant presence of vapor is present in the fluid. At block 350, the controller 150 sends a control signal to the control valve 130 directing the control valve 130 to provide increased back pressure to the fluid. The increased back pressure causes the vapor in contact with the cooler liquid to condense into a liquid state and prevents the fluid from flashing.

In a particular embodiment, controller 150 can use the drop in output signal amplitude as part of a proportional-integralderivative control routine to generate a control signal for a continuously variable control valve 130. The position of the aperture of continuously variable control valve 130 is modulated to gradually open or close depending on the output signal amplitude of the mass flow meter 120. For instance, if a liquid+vapor mixture is detected in the fluid from a drop in output signal amplitude, the position of the aperture of control valve 130 can be gradually closed to provide an increased back pressure on the fluid. As the output signal amplitude returns to normal, the position of the aperture of the control valve 130 can be gradually opened. This process can continue until the control valve 130 achieves an optimum flow setting providing for maximum flow allowable with enough back pressure to keep the fluid in a liquid state. Preferably, the control methodology should be configured to prevent the control valve 130 from operating in a completely closed position to allow for entrapped bubbles of vapor to flow out of the mass flow meter.

By making adjustments to control valve 130 in response to the presence of vapor in the fluid flowing in mass flow meter 120, the methodology 300 can reduce the presence of vapor in the fluid during mass flow and other measurements. This increases the accuracy of the mass flow and other measurements performed by mass flow meter 120 and can lead to more accurate and efficient inventory management of the fluid flowing in flow measurement system 100. Moreover, the embodiments of the present technology can be implemented using a minimal amount of equipment (e.g., mass flow meter, controller, and control valve) with minimal cost. In addition, as discussed below, embodiments of the present technology can perform other functions that complement and enhance the flow measurement of the fluid.

Figure 4:
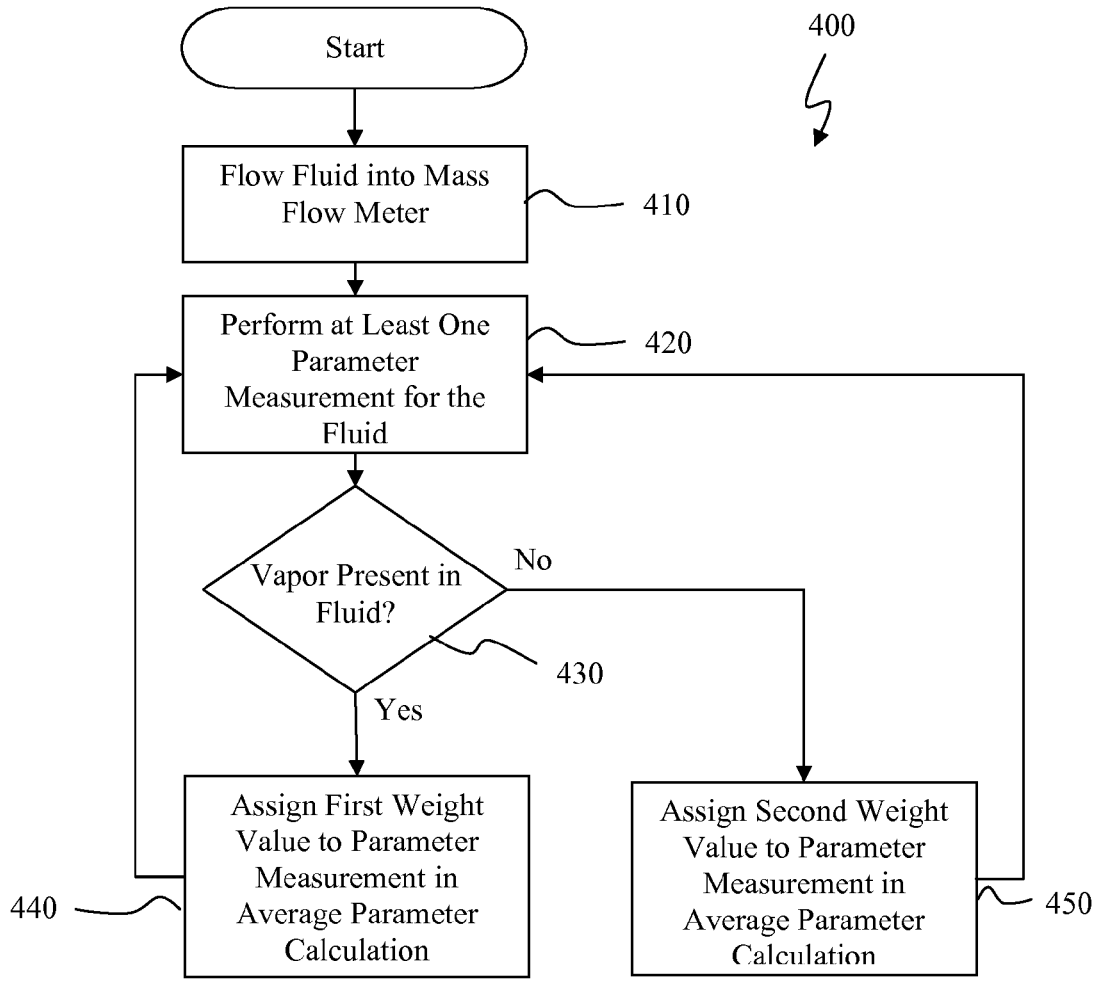
FIG. 4 provides a flow diagram of an exemplary method according to one embodiment of the present disclosure.

For example, with reference to FIG. 4, another exemplary embodiment of the present disclosure for performing an average parameter calculation will be discussed in detail. Utilizing a similar principle of vapor detection, the methodology 400 provides for improved average parameter value calculations, such as average density calculations and equivalent liquid volumetric calculations, for a fluid flowing in flow measurement system 100.

At block 410, fluid is provided into a mass flow meter. At block 420, the mass flow meter performs a parameter measurement for the fluid. For instance, a mass flow meter can perform a mass flow and/or a density measurement for the fluid. As will be discussed in additional detail below, the parameter measurement can be used in an average parameter calculation, such as an average net density calculation, that assigns a weight to a particular parameter measurement based on whether a vapor is determined to be present in the fluid flowing in the mass flow meter.

At block 430, the methodology 400 determines whether a vapor is present in the fluid flowing in the mass flow meter. In one embodiment, this determination can be made based at least in part on the amplitude of the output signal provided by the mass flow meter. As discussed above, the amplitude of the output signal(s) provided by a Coriolis mass flow meter is inversely proportional to the concentration of the minority fluid flowing in the mass flow meter. If a significant vapor is present in the fluid, the amplitude of the output signal provided by the mass flow meter decreases. Such a decrease in output signal amplitude can signify that less weight (emphasis) is applied in the averaging of the liquid's density under these conditions.

In another embodiment, the methodology 400 can determine whether a vapor is present in the fluid flowing in mass flow meter 120 by monitoring the driver signal provided to the flow tubes of a Coriolis mass flow meter. As discussed above, the driver signal causes the meter tubes of a Coriolis mass flow meter to vibrate. When the amplitude of vibration of the meter tubes decreases due to the presence of a vapor, the driver signal will increase in intensity in order to try to maintain the operating amplitude for the meter tubes. However, there is a limit on the amount of energy or gain that can be provided by the driver signal to the flow tubes of a Coriolis mass flow meter. A driver signal that has reached its limit on the amount of energy or gain that can be provided to the flow tubes of a Coriolis mass flow meter is considered to be saturated. When the amplitude of vibration decreases beyond a certain point, the driver signal will no longer be able maintain the operating amplitude for the meter tubes, sending the driver signal into saturation. If the driver signal for a Coriolis mass flow meter becomes saturated, the methodology 400 can determine that there is enough vapor present in the fluid flowing in mass flow meter 120 to stop averaging and to retain the weighted average value up to this point.

The methodology 400 assigns a weight value to the parameter measurement based at least in part on whether a vapor is present in the fluid flowing in the mass flow meter. A parameter measurement having a relatively large weight value will more significantly affect the average parameter calculation than a parameter measurement having a small weight value. As shown at block 440, if a vapor is determined to be present in the fluid flowing in the mass flow meter, the methodology 400 assigns a lower weight value to the parameter measurement. At block 450, if a vapor is determined not to be present in the fluid flowing in the mass flow meter, the methodology 400 assigns a higher weight value to the parameter measurement.

In accordance with embodiments of the present technology, the first weight value is less than the second weight value. For instance, in particular embodiments the first weight value can be zero and the second weight value can be a value that is greater than zero. In this manner, the methodology 400 provides for an average parameter measurement that is more heavily based on parameter measurements performed when a vapor is not detected in the fluid flowing in the mass flow meter.

The average parameter calculation can be for a variety of parameters of the fluid flowing in the mass flow meter. For instance, in one embodiment, the average parameter calculation is an average density calculation. The average density calculation can be used to provide an equivalent liquid volume calculation by dividing the total measured mass of the fluid by the average density calculated according to the methodology 400 discussed above. Such equivalent liquid volume calculation provides enhanced accuracy because it is based on an average density calculation that discounts density measurements performed when a vapor is detected in the fluid flowing in the mass flow meter.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure is not intended to preclude inclusion of such modifications, variations and/or additions to the present subject matter as would be readily apparent to one of ordinary skill in the art.

What is claimed is:

1. A method of determining an average parameter value of a fluid, the method comprising:
    flowing fluid in a mass flow meter;

measuring at least one parameter value for the fluid flowing in the mass flow meter;

determining whether a vapor is present in the fluid flowing in the mass flow meter;

assigning a weight value to the at least one parameter value based at least in part on the presence of a vapor in the fluid flowing in the mass flow meter; and calculating an average parameter value using the at least one parameter value and the weight value assigned the at least one parameter value.

2. The method of claim 1, wherein the step of assigning a weight value comprises:

assigning a first weight value to the at least one parameter value if a vapor is determined to be present in the mass flow meter; and assigning a second weight value to the at least one parameter value when a vapor is not determined to be present in the mass flow meter, wherein the first weight value is less than the second weight value.

3. The method of claim 1, wherein:

the mass flow meter is a Coriolis mass flow meter; and the step of determining whether a vapor is present in the mass flow meter comprises:

monitoring a driver signal provided to the Coriolis mass flow meter, determining whether the driver signal is saturated to determine that no further averaging should take place, and determining that a vapor is present in the fluid flowing in the Coriolis mass flow meter when the driver signal is saturated.

4. The method of claim 1, wherein the average parameter value comprises the average density of the fluid flowing in the mass flow meter.

5. The method of claim 4 wherein the method further comprises;

measuring the total mass of the fluid flowing in the mass flow meter, and determining an equivalent liquid volume value from the average density of the fluid flowing in the mass flow meter by dividing the average density by the total mass flowing in the mass flow meter.

6. The method of claim 2, wherein the first weight value is approximately zero.

\* \* \* \* \*